US010139391B2

United States Patent
Hou et al.

(10) Patent No.: US 10,139,391 B2
(45) Date of Patent: Nov. 27, 2018

(54) EJECTION STRUCTURE AND CONNECTOR WITH EJECTION MECHANISM

(71) Applicant: TAIDOC TECHNOLOGY CORPORATION, New Taipei (TW)

(72) Inventors: Hui-Sheng Hou, New Taipei (TW); Yi-Hsin Huang, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 105 days.

(21) Appl. No.: 14/931,995

(22) Filed: Nov. 4, 2015

(65) Prior Publication Data

US 2016/0123954 A1    May 5, 2016

(30) Foreign Application Priority Data

Nov. 5, 2014   (TW) ............................. 103138298 A

(51) Int. Cl.
  *A61B 5/15*   (2006.01)
  *A61B 5/145*   (2006.01)
  *A61B 5/157*   (2006.01)
  *G01N 33/487*   (2006.01)

(52) U.S. Cl.
  CPC ......... *G01N 33/4875* (2013.01); *A61B 5/157* (2013.01); *A61B 5/150022* (2013.01); *A61B 5/150358* (2013.01); *G01N 33/487* (2013.01); *A61B 5/14532* (2013.01)

(58) Field of Classification Search
  CPC .. G01N 33/4875; G01N 33/487; A61B 5/157; A61B 5/150022; A61B 5/150358; A61B 5/14532
  See application file for complete search history.

(56) References Cited

U.S. PATENT DOCUMENTS

| | | | | |
|---|---|---|---|---|
| 6,106,780 A * | 8/2000 | Douglas | ............. | A61B 5/14532 422/404 |
| 6,200,442 B1 * | 3/2001 | Markart | ............. | G01N 33/4875 204/400 |
| 7,449,148 B2 * | 11/2008 | Matsumoto | ............ | G01D 11/24 29/592 |
| 7,585,464 B2 * | 9/2009 | Amano | ............. | G01N 33/48757 204/400 |
| 2005/0256382 A1 * | 11/2005 | Eisenmann | ........ | G01N 33/4875 600/309 |
| 2006/0133956 A1 * | 6/2006 | Hamanaka | ................ | B01L 9/52 422/68.1 |
| 2009/0041631 A1 * | 2/2009 | Cho | .................... | A61B 5/14532 422/400 |

(Continued)

*Primary Examiner* — Lore R Jarrett

(74) *Attorney, Agent, or Firm* — Chun-Ming Shih

(57) ABSTRACT

An ejection structure includes a connector and an ejection element. The connector includes an opening and an ejection guiding groove for ejecting. The opening is received a biosensor test strip. The ejection guiding groove is disposed on a side of the connector and a front end of the guiding groove is communicating with the opening for receiving the biosensor test strip. The ejection element is assembled in the ejection guiding groove and comprises an actuating part used for contacting the biosensor test strip then ejecting the biosensor test strip along the ejection guiding groove from a rear end to the front end. Therefore, it omits extra assembled elements and simplifies the ejection structure so as to enhance the smoothness of the ejection mechanism.

8 Claims, 9 Drawing Sheets

(56) References Cited

U.S. PATENT DOCUMENTS

2010/0319170 A1* 12/2010 Hsu .................... G01N 33/4875
    24/457
2011/0143562 A1* 6/2011 Wu .................... A61B 5/14532
    439/152
2012/0126082 A1* 5/2012 Hsu .......................... B01L 9/52
    248/316.4

* cited by examiner

EJECTION STRUCTURE AND CONNECTOR WITH EJECTION MECHANISM

BACKGROUND OF THE INVENTION

Field of the Invention

The invention relates to an ejection structure and a connector with ejection mechanism. In particular, it relates to an ejection structure of the biosensor test strip, especially to a connector with an ejection guiding groove on a single main body.

Description of the Related Art

With the advance of today's technology and lifestyle changes, we used to do some examinations specific in the hospital, but now we only need to do it at home. Particularly to the changes of lifestyle brings about the increasing number of the patients with chronic diseases, and therefore accelerated the development of this industry. Wherein the blood glucose measurement is an important examination item, and measuring blood glucose concentration in the blood is a more important step to monitor and treat diabetes effectively.

The biosensor devices which currently sell on the market can use for measuring the content of the analyte in the liquid. It can measure the content of cholesterol, uric acid, protein, blood glucose, and glycated hemoglobin etc. in the specimen, wherein the specimen can be whole blood, plasma, serum, urine, tissue fluid etc., and then measured with electrochemical biosensor test strips and biosensor devices. There is a connector in the biosensor device used for receiving an electrochemical biosensor test strip, and conductively connecting the electrochemical biosensor test strips and biosensor devices via the connection of the connector. Normally this kind of biosensor test strip is disposable, and you will need to eject the electrochemical biosensor test strips from the connector after measurement process has been finished.

A conventional ejection structure of the connector is usually composed together with multiple parts. In addition to a pushing element which has to apply external force by the user, it further needs additional auxiliary sliding element to assemble together with the connector main body and pushing element to achieve the purpose of test strip ejection. The complexity of the structure will increase assembling error, manufacturing cost of the parts and also time consuming. Especially after prolonged use, there are possibilities that any loss of assembly workpiece will lead to ejection mechanism failure, and the more failure risks of the ejection mechanism occurred by the complexity structure will reduce service life of the products.

Besides, the demands of today's biosensor device for users to carry are lightweight and easy to use. And if the connector assembled by multiple workpieces, the structure of the connector is not only complex, but also increasing its size, and it will limit the shrinkable size of the biosensor device, moreover the bulky connector design will impede market demands.

Therefore, for how to shrink the main body size of the connector, enhance the yield of ejection mechanism operation, and reduce the manufacturing cost of the ejection structure workpieces are what the manufacturers need to be further improved.

SUMMARY OF THE INVENTION

In order to improve the conventional deficiencies above, the present invention provides an ejection mechanism, it uses single ejection element to slide in an ejection guiding groove of a connector. It omits the additional assembled sliding element, and reduces the manufacturing cost of the whole ejection structure parts.

The present invention provides an ejection structure, it is assembled with a single workpiece in the ejection guiding groove of the connector to achieve the effectiveness of ejection, simplified the complex assembly structure of ejection workpieces, and enhance the smoothness of the ejection mechanism operation.

The present invention provides a connector with ejection mechanism, it uses the actuating part of the ejection element to insert into the ejection guiding groove which is disposed at a lateral of the main body of the connector to achieve the purpose of ejection, and significantly reduced the size of the main body of the connector.

In order to achieve the purpose above, the present invention provides an ejection structure disposed on a biosensor device, comprising:

a connector comprising an opening and an ejection guiding groove, the opening used for receiving a biosensor test strip, the ejection guiding groove disposed on a side of the connector, and a front end of the ejection guiding groove communicating with the opening to receive the biosensor test strip; and an ejection element assembled with the ejection guiding groove and comprising an actuating part, the actuating part used for contacting the biosensor test strip, and then ejecting the biosensor test strip along the guiding groove from a rear end to the front end of the ejection guiding groove.

In an embodiment in accordance with the present invention, the connector is integrally molded.

In an embodiment in accordance with the present invention, the connector comprises a first side and a second side, the first side disposed on a circuit board of the biosensor device, the second side faced to the first side, and the ejection guiding groove disposed on the second side of the connector. In an embodiment in accordance with the present invention, the ejection guiding groove is not disposed to communicate with the first side of the connector.

In an embodiment in accordance with the present invention, the connector can further comprise a terminal group for allowing the connector electrically connected to the circuit board.

In an embodiment in accordance with the present invention, the ejection guiding groove can be parallel opposing two guiding grooves which are stair type grooves.

In an embodiment in accordance with the present invention, the actuating part can be inverse stair type which is corresponding to stair type ejection guiding groove.

In an embodiment in accordance with the present invention, the ejection element is integrally molded.

In an embodiment in accordance with the present invention, the ejection element can further comprise a trigger connected to the actuating part, and when the trigger actuated by an external force, it leads the actuating part moving inside the ejection guiding groove.

In an embodiment in accordance with the present invention, the ejection element can further comprise an elastic part to make the ejection element restore by axially moving.

In an embodiment in accordance with the present invention, the biosensor device can be used for detecting blood glucose.

From another point of view, the present invention provides a connector assembled on a circuit board, comprising:

an opening used for receiving a biosensor test strip;

an ejection guiding groove disposed on a side of the connector, and a front end of the ejection guiding groove communicating with the opening to receive the biosensor test strip; and an ejection element assembled with the ejection guiding groove, and comprising an actuating part used for contacting the biosensor test strip, and then ejecting the biosensor test strip along the guiding groove from the rear end to the front end.

In an embodiment in accordance with the present invention, the connector can further comprise an electrical conductor disposed around the connector to prevent the electrical interference to the connector from outside. In an embodiment in accordance with the present invention, the electrical conductor can be made by metal.

In an embodiment in accordance with the present invention, the electrical conductor can further comprise an assembly hole to let the connector assembled on the circuit board by a Surface Mounted Technology (SMT).

Based on the set forth above, the ejection structure and the connector therewith in accordance with the present invention respectively comprises the ejection guiding groove disposed at a lateral of the body and assembled with the ejection element to axially move along the ejection guiding groove for achieving the purpose of ejection. It not only reduces the assembling error of the ejection structure and manufacturing cost, enhances the smoothness of the ejection mechanism operation, but also shrinks the main body size of the connector at the same time, meets the lightweight demand of biosensor devices, and increases its design convenience.

In order to make the features and the advantages more realizable in the present invention, the following description and accompanying drawings are some examples in accordance with the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENTS

Figure 1A:
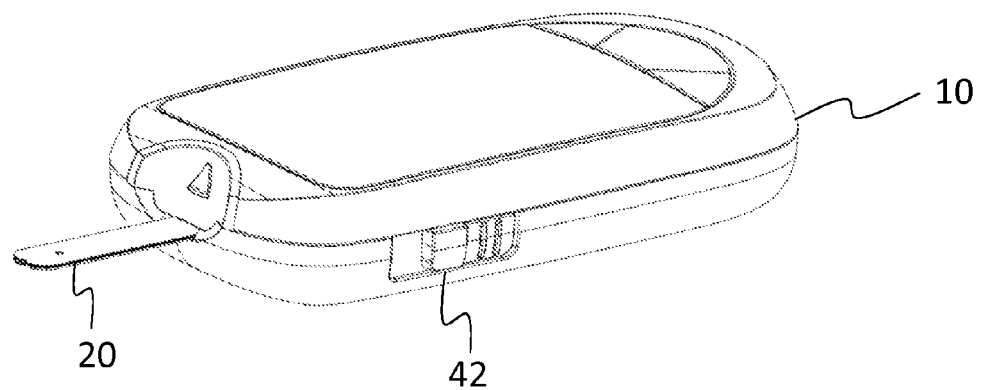
FIG. 1A shows a preferred embodiment of a biosensor test strip assembled in a biosensor device according to the present invention in a schematic view.

A conventional connector and its corresponding ejection structure usually consists of a plurality of workpieces, and it's not only bulky but also prone to error when assembled. After prolonged use by the users, there is possibility that any loss of assembly workpiece will lead to ejection mechanism failure, especially the more assembly workpieces it has, the more risks of ejection mechanism failure will occur. In the meanwhile, it increases manufacturing cost, and it doesn't meet the lightweight demand of assembled products, furthermore it reduces the competitiveness of products.

On the contrary, an embodiment of an ejection mechanism in accordance with the present invention through disposed an ejection guiding groove at a lateral of a connector to the corresponding ejection element which is directly making axially move along the ejection guiding groove to achieve the purpose of ejection. It doesn't need to assemble additional sliding element so as to avoid the risk of ejection mechanism failure because the loss of multiple workpieces, and also can shrink the size of the connector. The following detailed description and accompanying drawings are some examples in accordance with the present invention. The same symbol herein in the drawings indicates the same or similar structure.

Figure 1B:
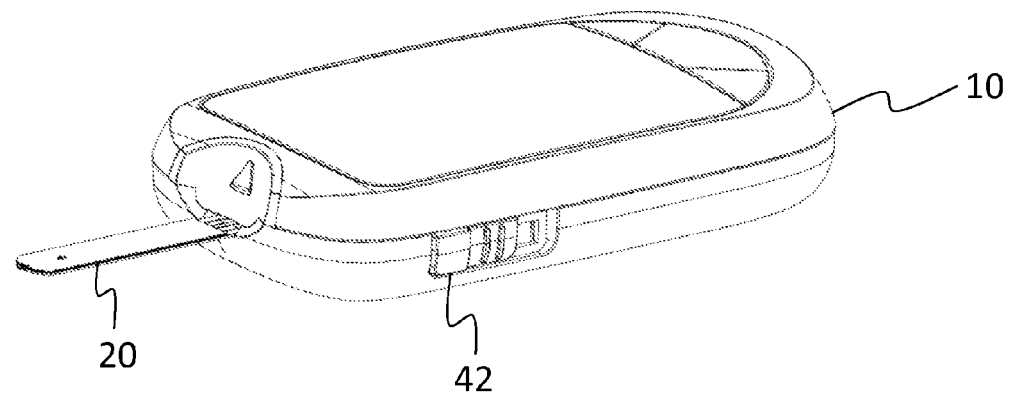
FIG. 1B shows a preferred embodiment of the biosensor test strip ejected from the biosensor device according to FIG. 1A of the present invention in a schematic view.

FIG. 1A shows a preferred embodiment of a biosensor test strip assembled in a biosensor device according to the present invention in a schematic view. FIG. 1B shows a preferred embodiment of the biosensor test strip ejected from a biosensor device according to FIG. 1A of the present invention in a schematic view. Please refer to FIGS. 1A and 1B in combination. In accordance with the present embodiment, the present invention provides an ejection structure assembled in a biosensor device (10) used for receiving a biosensor test strip (20) to detect the concentration of an analyte in a sample. Preferably, the biosensor test strip (20) is an electrochemical biosensor test strip, and the sample is in a liquid phase, and more preferably, the sample is liquid obtained from human body. The analyte species of the biosensor device (10) detected can be included but not limited to the blood glucose, blood glycosylated hemoglobin, ketones, urine protein or other subjects of liver function test. Preferably, the biosensor device is a blood glucose meter, but the present invention shall not be limited in this.

Figure 2A:
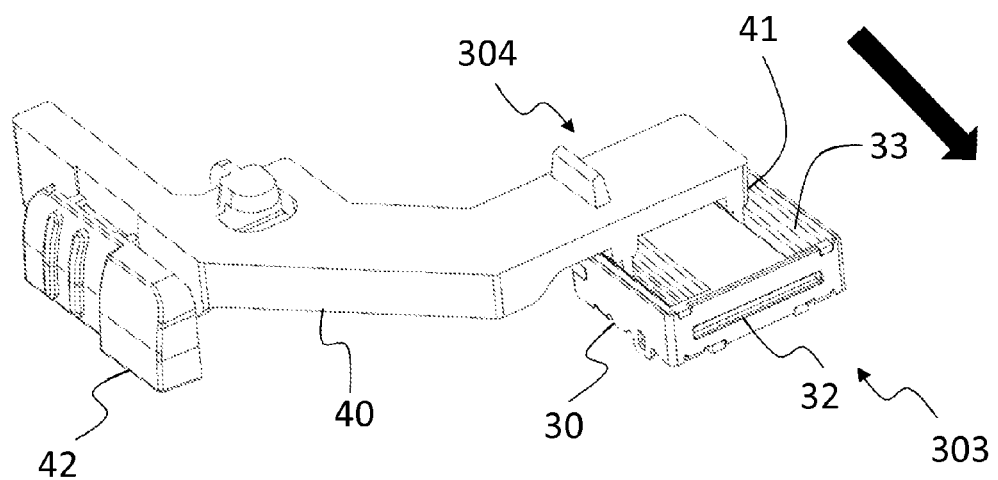
FIG. 2A shows a preferred embodiment of an ejection structure before ejecting according to the present invention in a schematic view.
Figure 2B:
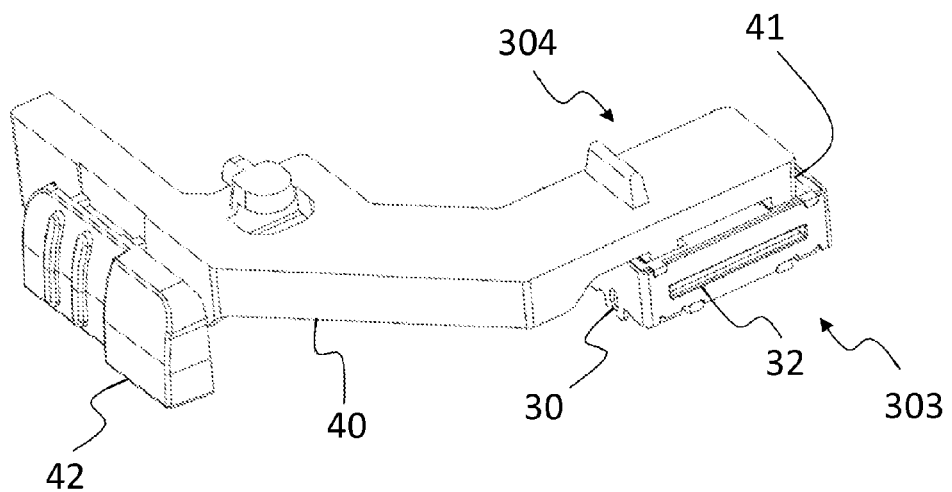
FIG. 2B shows a preferred embodiment of an ejection structure after ejecting according to the present invention in a schematic view.
Figure 3A:
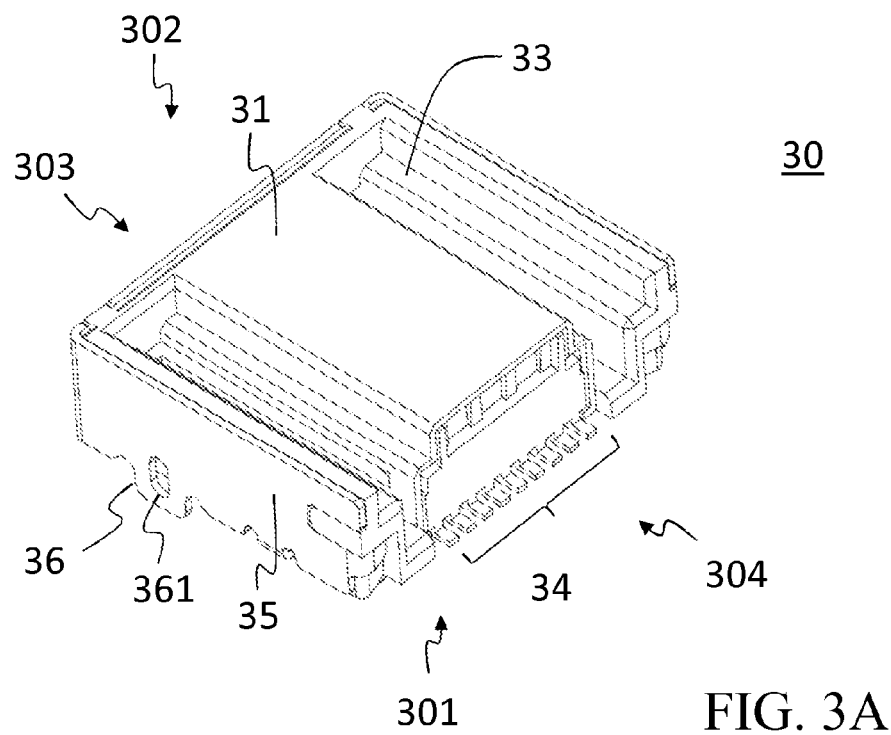
FIG. 3A shows a preferred embodiment of a connector according to the present invention in a schematic perspective view.
Figure 3B:
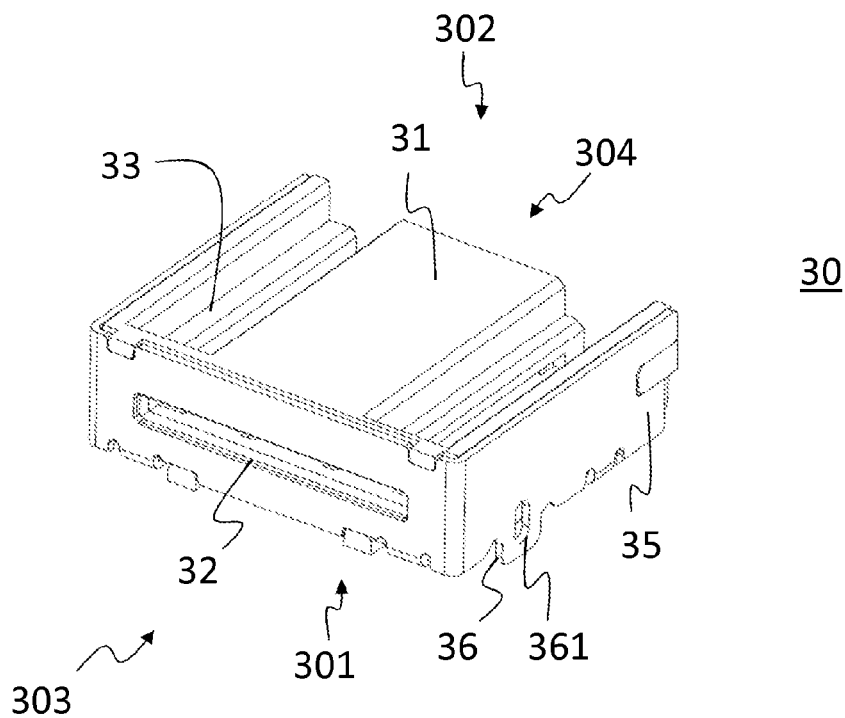
FIG. 3B shows another side of the connector according to FIG. 3A in a schematic perspective view.

FIG. 2A shows a preferred embodiment of an ejection structure before ejecting according to the present invention in a schematic view. FIG. 2B shows a preferred embodiment of an ejection structure after ejecting according to the present invention in a schematic view. Please refer to FIGS. 2A and 2B in combination. The ejection structure comprises a connector (30) and an ejection element (40), and the following will use the connector for the first further description. FIG. 3A shows a preferred embodiment of a connector according to the present invention in a schematic perspective view. FIG. 3B shows another side of the connector according to FIG. 3A in a schematic perspective view. Please refer to FIGS. 1A to 3B in combination. The connector (30) comprises a main body (31), preferably, it's made by plastic and integrally molded. In terms of the orientation of the connector (30), the connector (30) comprises a first side (301), a second side (302), a front end (303), and a rear end (304). The first side (301) faced to the second side (302), the front end (303) faced to the rear end (304). In terms of the structure of the connector (30), the connector (30) comprises an opening (32) and an ejection guiding groove (33).

Figure 6A:
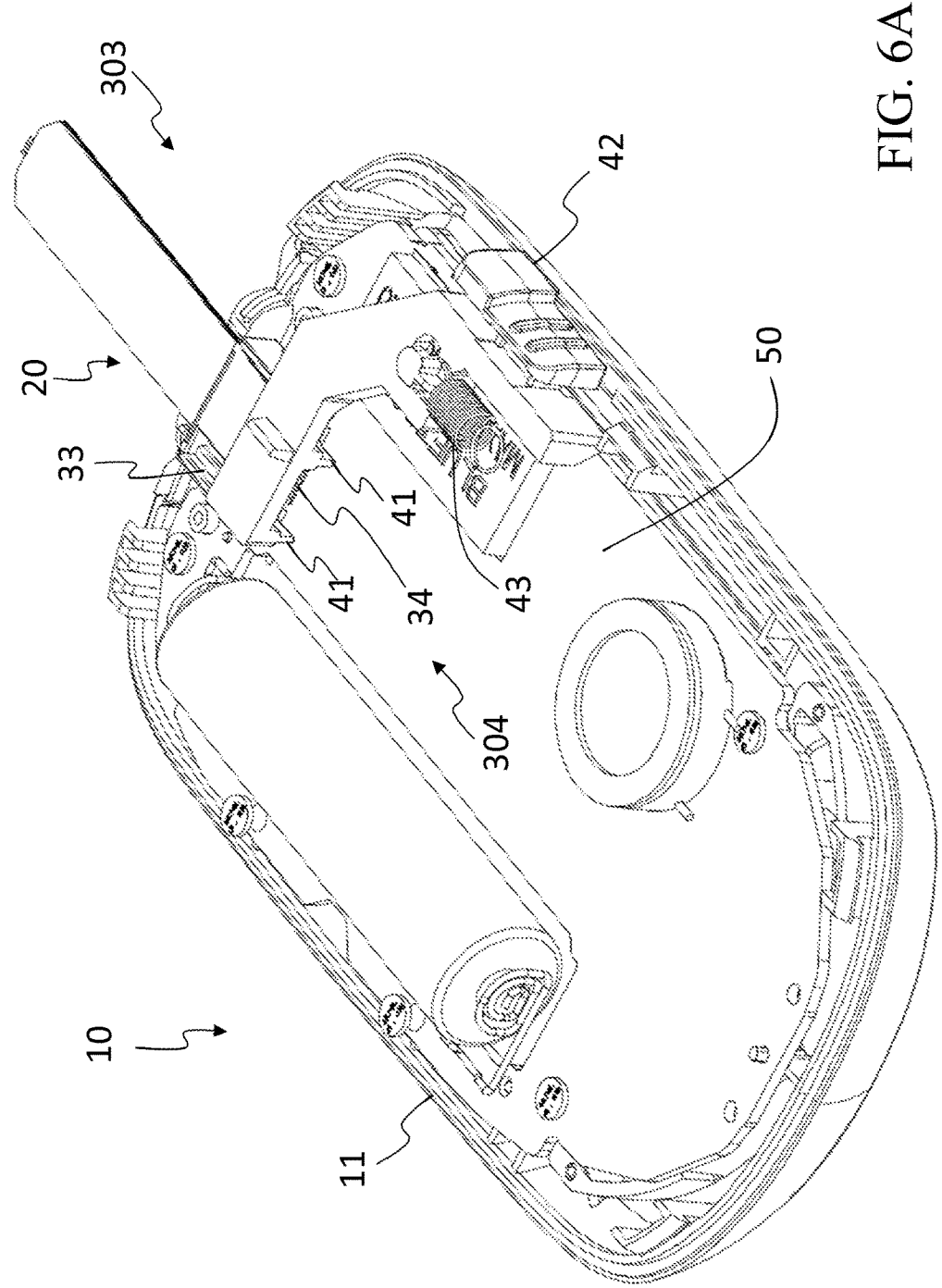
FIG. 6A shows a preferred embodiment of the biosensor device according to FIG. 1A of the present invention when ejection in a schematic view.

Preferably, the first side (301) of the connector (30) is assembled on a circuit board (50) of the biosensor device (10) (as shown in FIG. 6A), preferably, the circuit board (50) is a printed circuit board (PCB). The ejection guiding groove (33) is disposed at the second side (302) of the connector (30), preferably, the ejection guiding groove (33) is not disposed to communicate with the first side (301). The ejection guiding groove (33) is assembled with the ejection element (40) to achieve the purpose of ejecting the biosensor test strip (20), and the ejection mechanism will be described in detail later. More specifically, the ejection guiding groove (33) is recessed of the main body (31) of the connector (30) in the groove-like structure, preferably, the ejection guiding groove (33) is a double guiding grooves and disposed at the two inner sides of the main body (31) of the connector (30), and it can be opposing parallel double guiding grooves. More preferably, the ejection guiding groove (33) is a ladder or stair type guiding groove, wherein the design of parallel double guiding grooves make the ejection element (40) apply force to push the biosensor test strip (20) in the ejection guiding groove (33) more evenly, and enhance the smoothness of the ejection operation.

The opening (32) is used for receiving the biosensor test strip (20), and it is disposed to communicate with the ejection guiding groove (33), preferably, the opening (32) is a transverse opening disposed at the front end (303) of the connector (30). More specifically, the biosensor test strip (20) is received from the opening (32) of the connector (30), and then receive in the ejection guiding groove (33).

Figure 4:
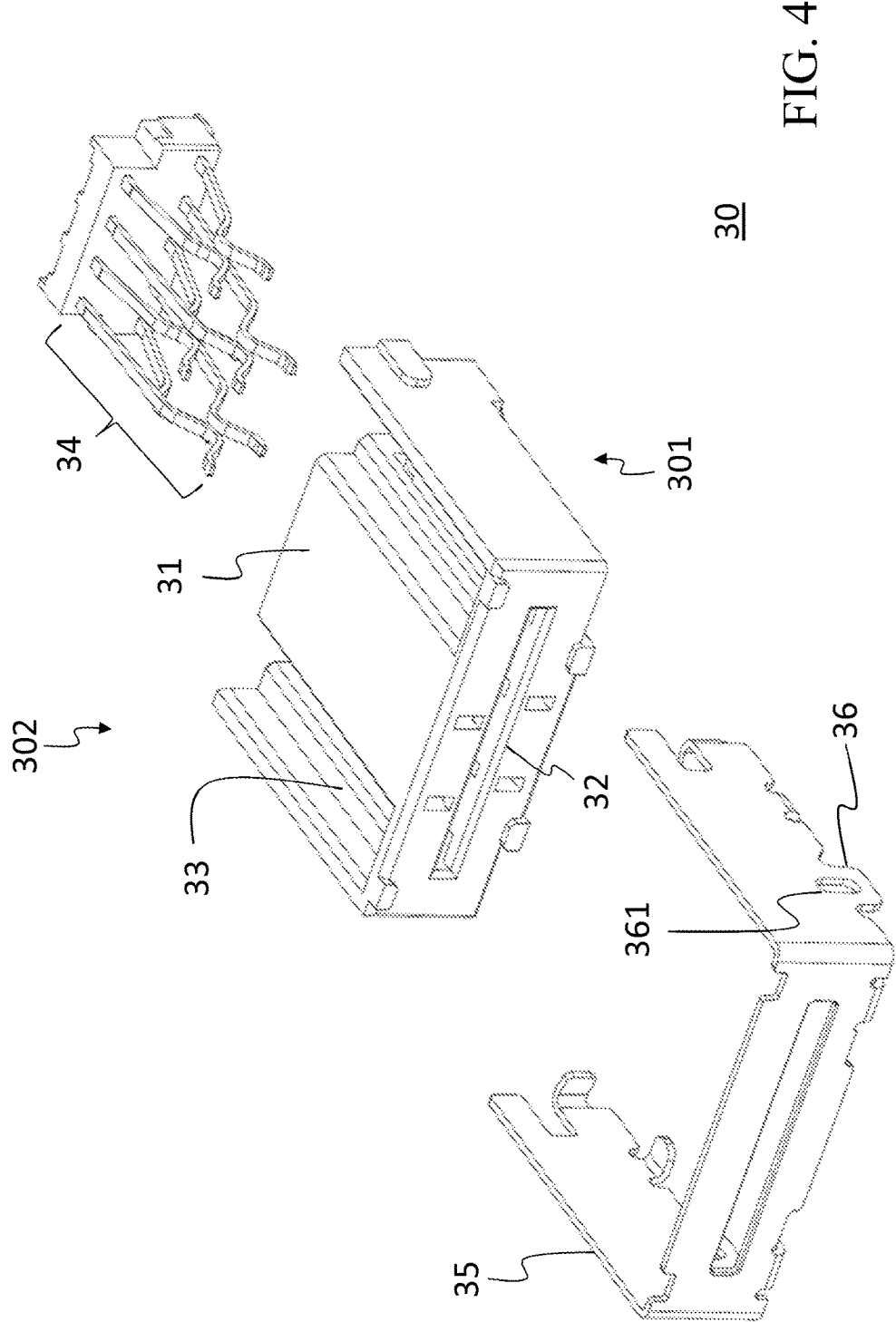
FIG. 4 shows a preferred embodiment of the connector according to FIG. 3A of the present invention in an exploded perspective view.

FIG. 4 shows a preferred embodiment of the connector according to FIG. 3A of the present invention in an exploded perspective view. Please further refer to FIG. 4, the connector (30) can further comprise a terminal group (34) for allowing the connector (30) electrically connected to the circuit board (50) (as shown in FIG. 6C), preferably, the terminal group (34) is consisted by a plurality of metal terminals. More specifically, when the biosensor test strip (20) is receiving in the ejection guiding groove (33), the terminal group (34) will contact with an end of the biosensor test strip (20) and applying a voltage to the biosensor test strip (20) through the circuit board (50) for detecting the electrical changes to obtain the concentration of the analyte. Preferably, the terminal (34) is parallel disposed between the double ejection guiding grooves.

The connector (30) further comprises an electrical conductor (35) disposed around the connector (30) to prevent the electrical interference to the connector (30) from outside. Preferably, the electrical conductor (35) is made by metal, more specifically, the electrical conductor (35) is cladded between a lateral of the first side (301) and the second side (302) of the connector (30). When there are possibilities of generating the electrostatic or other electrical changes from outside, it will enter through the opening (32) of the connector (30) or transmit from the terminal group (34) to impact other precision components on the circuit board (50). Especially when the impact of the transient electrical changes is too large, it even will burn out other electronic parts or cause malfunction. The electrical conductor (35) connects the ground wire by using its conductive property to avoid the affection to other electronic parts on the circuit board (50) because of the electronic changes from outside and transmitting by the connector (30).

Figure 6B:
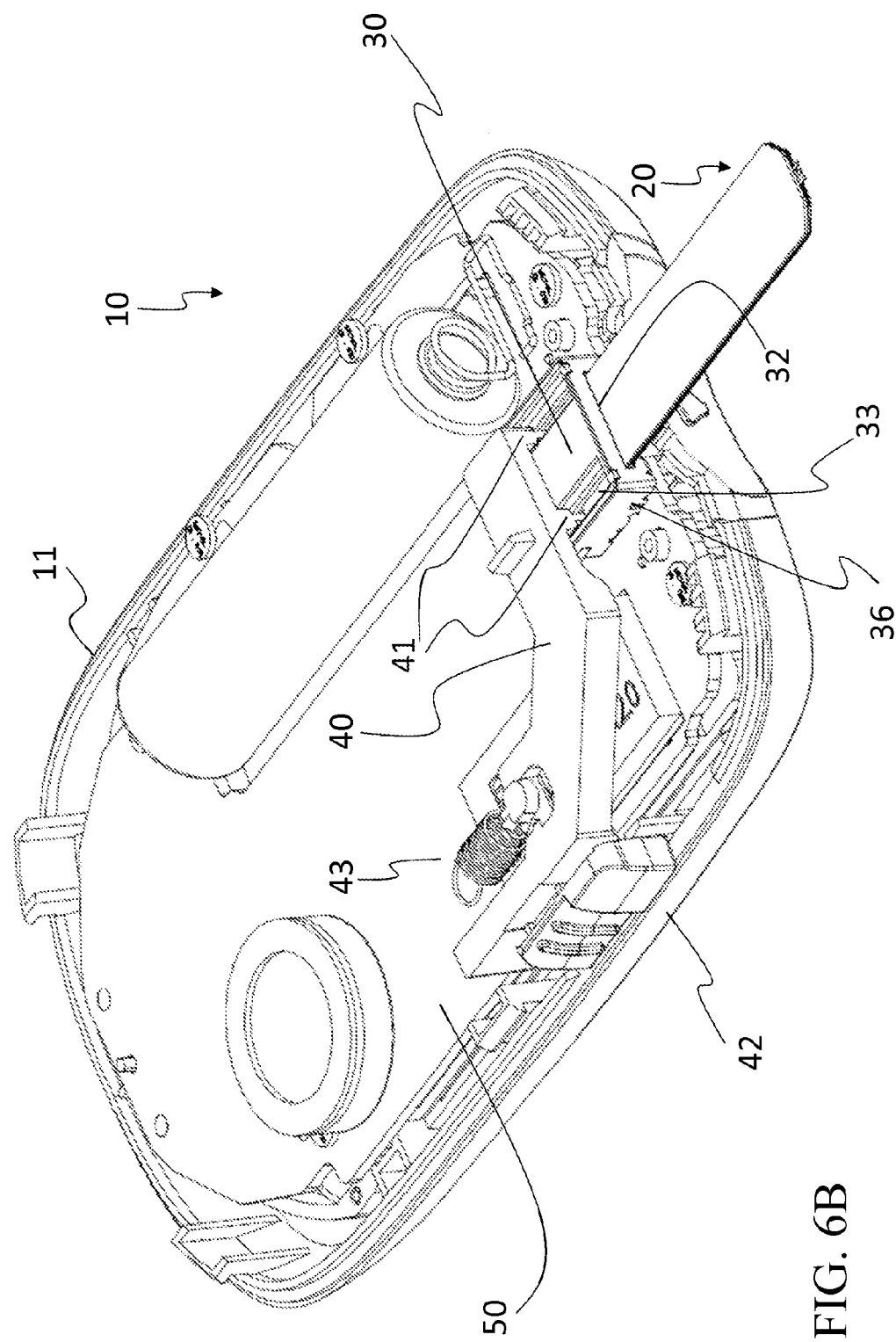
FIG. 6B shows another side of the biosensor device according to FIG. 6A in a schematic view.
Figure 6C:
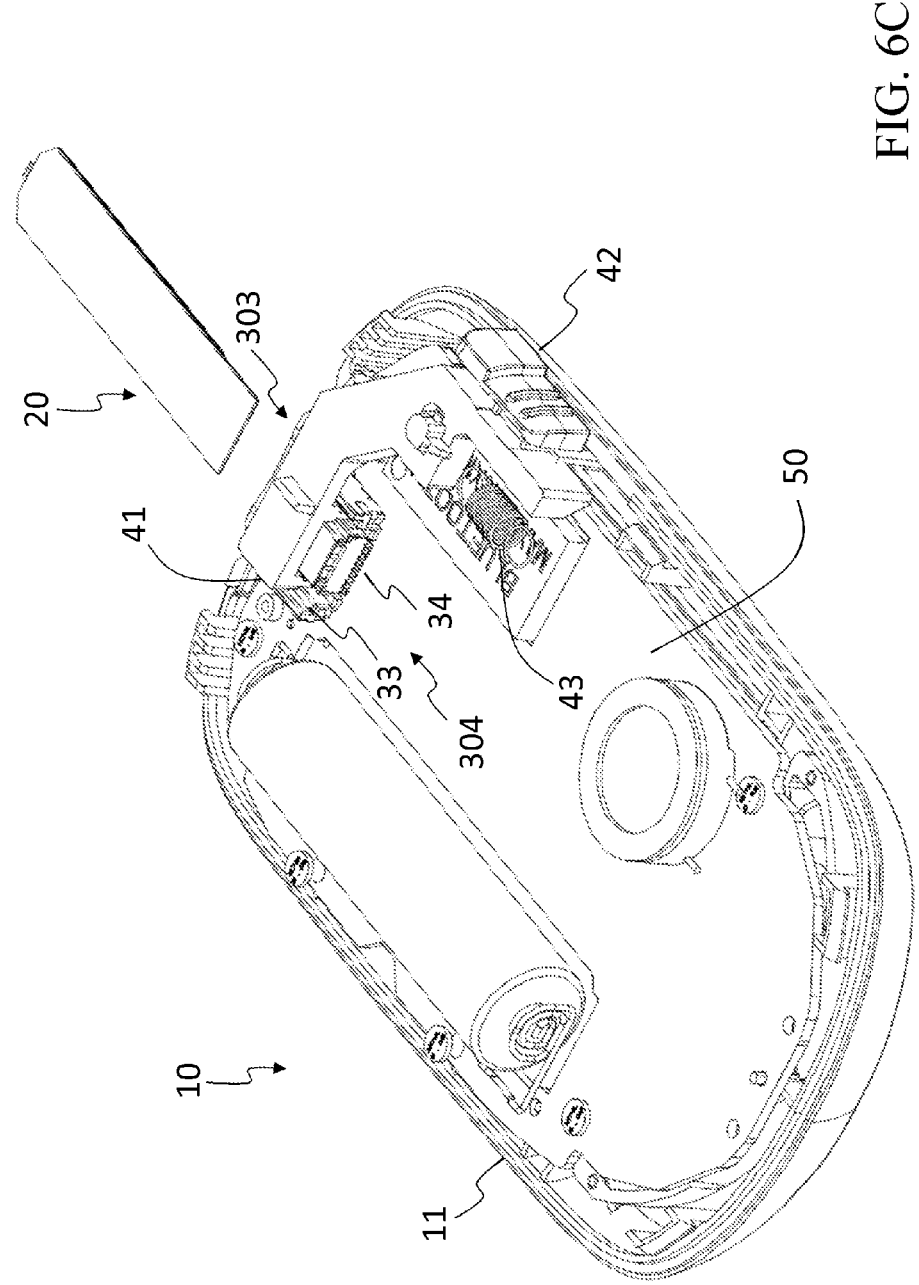
FIG. 6C shows a preferred embodiment of the biosensor device according to FIG. 1B of the present invention when ejection in a schematic view.

Preferably, the electrical conductor (35) is a surface mounted device (SMD) and further comprises an assembly hole (361) to strengthen the connectivity of the surface mounted device (SMD) assembled on the circuit board (50) (as shown in FIG. 6B). Preferably, there is a protrusion (36) on the electrical conductor (35) used for plugging on the circuit board (50), videlicet, the protrusion (36) is a protruding pin extended from the electrical conductor (35), preferably, the protrusion (36) is a flaky texture. The assembly hole (361) is disposed on the protrusion (36), and when the protrusion (36) is welded to the circuit board (50), the assembly hole (361) provided a solder flowing space penetrating the protrusion (36) and the circuit board (50) to achieve the purpose of strengthen the connectivity of the surface mounted device.

Figures 5A, 5B:
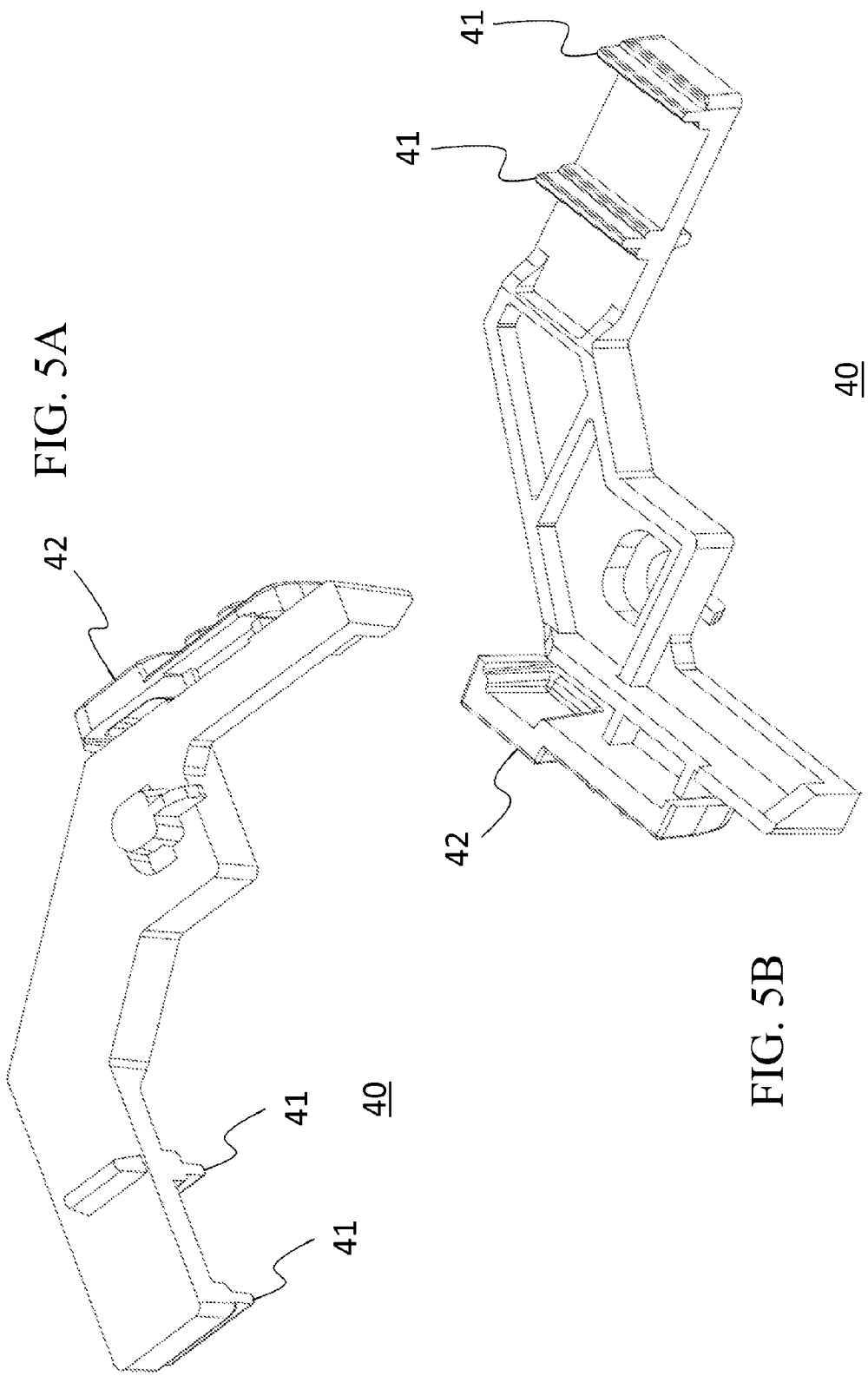
FIG. 5A shows a preferred embodiment of an ejection element according to the present invention in a schematic perspective view.
FIG. 5B shows another side of the ejection element according to FIG. 5A in a schematic perspective view.

FIG. 5A shows a preferred embodiment of an ejection element according to the present invention in a schematic perspective view. FIG. 5B shows another side of the ejection element according to FIG. 5A in a schematic perspective view. Please refer to FIGS. 1A to 5B in combination. The ejection element (40) is assembled with the ejection guiding groove (33) of the connector (30), preferably, the ejection element (40) is integrally molded, wherein the ejection element (40) comprises an actuating part (41), the actuating part (41) is used for contacting the biosensor test strip (20), then moved from the rear end (304) to the front end (303) along the ejection guiding groove (33) to eject the biosensor test strip (20) from the opening (32). Preferably, the shape of an actuating part (41) is corresponding to the shape of the ejection guiding groove (33), such as the stair type. More preferably, the actuating part (41) is two parallel stair type pushing blocks, but the present invention shall not be limited in this. Those skilled in the art can change the corresponding patterns and the amounts of the ejection guiding groove (33) and its related ejection element (40). It is worth mentioning that the ejection guiding groove (33) is disposed on a lateral of the connector (30), and the ejection guiding groove (33) is recessed in the groove-like structure of the main body (31) of the connector (30) to receive the ejection element (40). Therefore, comparing to a conventional moving element additional assembled on the main body (31) of the connector (30), the present design is significantly reduced the size of the connector main body, and remained the operation function of the ejection mechanism at the same time.

The ejection element (40) further comprises a trigger (42), the trigger (42) is connected to the actuating part (41), and when the trigger (42) actuated by an external force, it will lead the actuating part (41) moving inside the ejection guiding groove (33). More specifically, the trigger (42) is exposed at the outside of the biosensor device (10) to let the users apply force at the trigger (40) to provide the ejection element (40) an axially moving power. For example, the trigger (42) is a press or a push button.

The ejection element (40) further comprises an elastic part (43) (as shown in FIG. 6A to FIG. 6D), the elastic part (43) makes the ejection element (40) restore by axially moving, preferably, the elastic part (43) is a spring, but the present invention shall not be limited in this. For example, the elastic part (43) is connected between a case (11) of the biosensor device (10) and the trigger (42) of the ejection element (40).

When there is an external force applying at the trigger (42), the trigger (42) will lead the actuating part (41) moving toward to front end (303) from rear end (304) of the ejection guiding groove (33), and the elastic part (43) is a tensile state caused by the external force to generate a cohesive force. When the external force is removed from the trigger (42), the cohesive force from the elastic part (43) will make it restitution, thereby leading the actuating part (41) moving toward to rear end (304) from front end (303) of the ejection guiding groove (33) to achieve the purpose restoring position.

FIG. 6A shows a preferred embodiment of an ejection element inside the biosensor device according to FIG. 1A of the present invention when ejection in a schematic view. FIG. 6B shows another side of the biosensor device according to FIG. 6A in a schematic view. Please refer to FIGS. 1A, 2A, 6A and 6B in combination. In the present embodiment, firstly, when the users use the biosensor device (10) for detection, the biosensor test strip (20) is inserted into the connector (30) from the opening (32) and received in the ejection guiding groove (33). The biosensor test strip (20) is contacted with the terminal group (34) and detected the concentration of the analytes by electrically connected. At the meantime, the actuating part (41) of the ejection element (40) is positioned at the rear end (304) of the ejection guiding groove (33) and contacting with the biosensor test strip (20), and the trigger (42) isn't pushed by external force, and the elastic part (43) is in an un-tensile state.

Figure 6D:
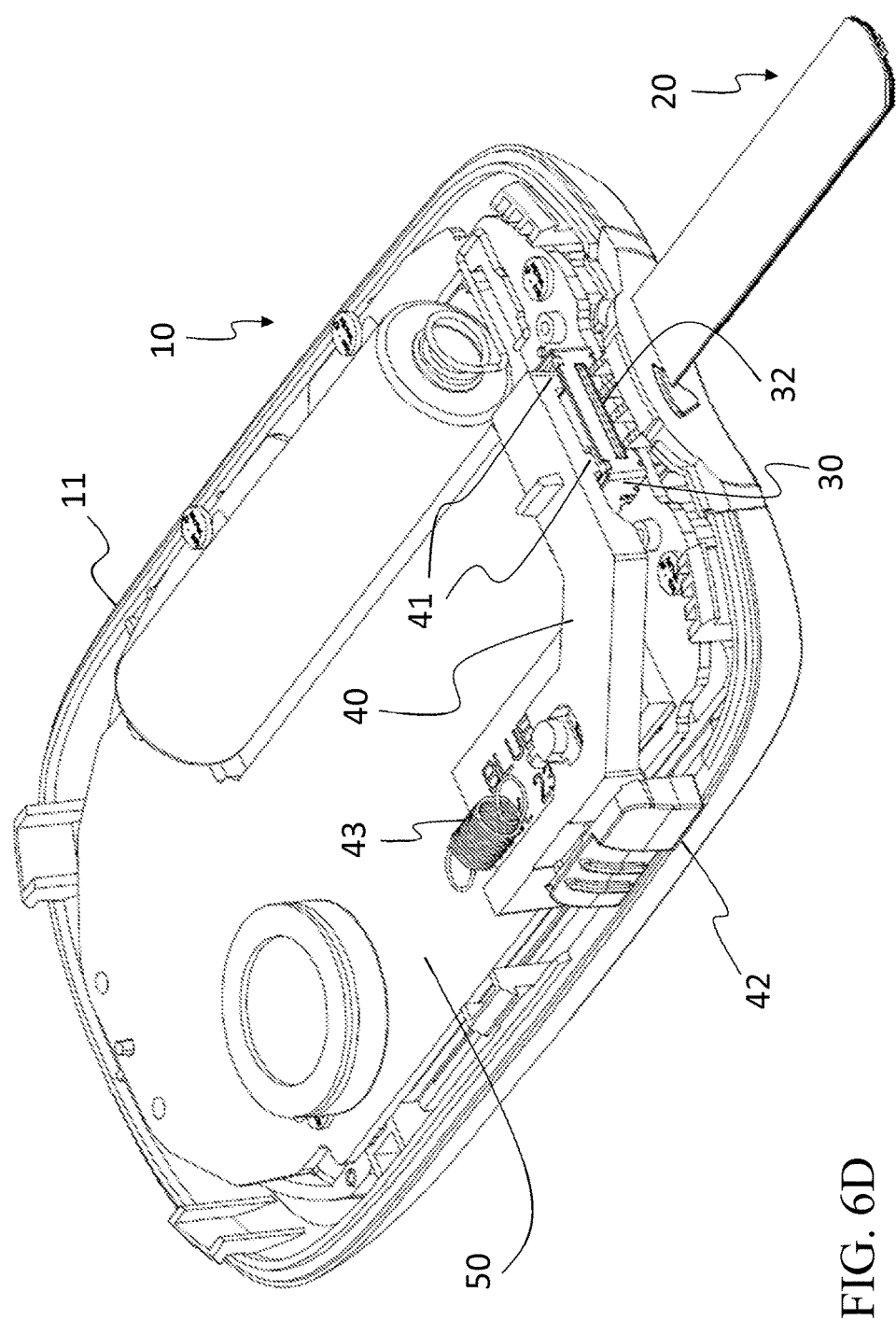
FIG. 6D shows another side of the biosensor device according to FIG. 6C in a schematic view.

FIG. 6C shows a preferred embodiment of the biosensor device according to FIG. 1B of the present invention when ejection in a schematic view. FIG. 6D shows another side of the biosensor device according to FIG. 6C in a schematic view. Please refer to FIGS. 1B, 2B, 6C and 6D in combination. The users eject the biosensor test strip (20) by applying force at the trigger (42) when the detection is completed, preferably, the trigger is pushed toward to the opening (32) of the connector (30) to lead the actuating part (41), and made the ejection element (40) move toward to the front end (303) from the rear end (304) of the ejection guiding groove (33), and the biosensor test strip (20) ejected from the opening (32) by axially moving along the ejection guiding groove (33). It is worth noting that sliding in the ejection guiding groove (33) of the main body (31) of the connector (30) via the single structure of the ejection element (40) to achieve the ejection mechanism of the biosensor test strip (20), omit additional assembled sliding element, enhance the smoothness of the ejection operation by an integrally molded structure, and reduce the risk of ejection mechanism failure because the loss of multiple workpieces to extend the service life of ejection structure.

Although the possible kinds of the ejection structure and the connector with ejection mechanism in accordance with the present invention has been described in the embodiments above, those skilled in the art shall recognized that the ejection structure and the connector with ejection mechanism from various manufacturers can be designed differently. Therefore, the spirit of the present invention shall not be limited to these possible kinds of ejection structure and the connector with ejection mechanism in accordance with the present invention. In other words, as long as the ejection structure comprises an ejection guiding groove from a single side of the connector main body to let the ejection element axially moving along the ejection guiding groove and omit multi workpieces assembly ejection structure to achieve the purpose of ejecting biosensor test strip which is the key spirit and scope of the present invention. The followings are some other embodiments in accordance with the present invention for those skilled in the art to know more about the spirit of the present invention.

According to the embodiment in accordance with the present invention in FIGS. 6A to 6D, the connector (30) is disposed at a circuit board (50) and comprises an opening (32), the opening (32) is used for receiving a biosensor test strip (20), and the ejection structure is assembled at a biosensor device (10), preferably, the biosensor device (10) is a blood glucose meter which is only an alternative embodiment of the present invention. Those skilled in the art can change the assembly connector and circuit board of other downstream applications as needed. In accordance with the other embodiments, the biosensor device can be smart mobile devices with biological sensing function, for example, smartphone, tablet PCs, smart bracelets or other portable electronic device with transmissive or communicative function.

Following the description above, the connector (30) is disposed at the circuit board (50), the ejection structure is assembled at the biosensor device (10) which is only an alternative embodiment of the present invention. Those skilled in the art can change the position of the connector. In accordance with the other embodiments, the ejection structure is a separated individual device connected with the biosensor device or other electronically device to achieve the purpose of detecting analytes on the biosensor test strip or ejecting the biosensor test strip.

Accordingly, the present invention is corresponding to an ejection structure and a connector with ejection mechanism, through disposed the ejection guiding groove at a lateral of the connector, and made an axially moving to eject the biosensor test strip by using single structure of the ejection element assembling on the ejection guiding groove, it's not only omitting a sliding element to simplify the ejection structure, but also enhance the smoothness of the ejection structure operation. Furthermore, there are also other advantages in some embodiments of the present invention exemplarily listed as follows:

1. The connector with ejection structure in accordance with the present invention comprising an ejection guiding groove disposed from a single side to receive a single structure of assembly ejection element, and the actuating part inserted into the ejection guiding groove make the axially movement achieve the purpose of ejection. Significantly reduce the size of the main body of the connector, increase the assembly product design space of the connector and enhance the market competitiveness of product applications.

2. The ejection structure in accordance with the present invention is using single ejection element sliding in the connector which has ejection guiding groove to achieve the purpose of ejection. Omit other unessential assembly workpieces and reduce the manufacturing costs of all ejection structure.

3. The peripheral of the connector is clad with the electrical conductor and connect the ground wire via its conductive property to isolate the electrostatic interference from the circuit board and prevent from burning other components on the circuit board.

4. The electrical conductor of the connector is provided with the design of an assembly hole, it's beneficial to the circuit board engagement by using Surface Mount Technology (SMT), and providing additional welding space to strengthen the connectivity between the structures.

Although the present invention has been disclosed the embodiments as above, it should be understood those are given by way of illustration only, those skilled in the art will recognize that the present invention can be practiced with modification within the spirit and scope of the claims.

What is claimed is:

1. A biosensor device for cooperating with a biosensor test strip via a connector disposed on a circuit board of the biosensor device to determine an analyte in a sample, the biosensor device comprising the connector and the connector comprising:
   a body having a first side disposed on the circuit board, a second side which is relative to the first side, a front end, and two lateral sides;
   an opening at the front end which is disposed between the first side and the second side of the body for receiving the biosensor test strip;
   an ejection guiding groove disposed on the second side of the body, and a front end of the ejection guiding groove communicating with the opening to contain one end of the biosensor test strip; and
   an electrical conductor formed of a unitary component made of metal, and attached to the front end, and two lateral sides of the body to prevent an electrical interference from outside of the connector; and
   an ejection element cooperating with the ejection guiding groove of the body, and comprising an actuating part slidely disposed in the ejection guiding groove such that the actuating part positioned at a rear end of the ejection guiding groove before ejecting the biosensor test strip and the actuating part positioned at the front end of the ejection guiding groove after ejecting the biosensor test strip.

2. The biosensor device as claimed in claim 1, wherein the body is formed in one piece.

3. The biosensor device as claimed in claim 1, wherein the ejection guiding groove is a stair type groove formed on the second side of the body.

4. The biosensor device as claimed in claim 1, wherein the ejection guiding groove has a central part and a lateral part, the central part communicates with the lateral part, the central part has a hollow space and a top surface to cover one end of the biosensor test strip, and the lateral part has two grooves paralleling to each other.

5. The biosensor device as claimed in claim 4, wherein the lateral part comprises a narrow groove and a wide groove, the narrow groove communicates with the wide groove.

6. The biosensor device as claimed in claim 1, wherein the electrical conductor further comprises an assembly hole to assemble the connector on the circuit board of a Surface Mounted Device (SMD).

7. The biosensor device as claimed in claim 1, further comprising a terminal group connected with the body, one end of the terminal group for contacting the biosensor test strip and the other end of the terminal group mounted on the circuit board.

8. A biosensor system, comprising: a biosensor test strip; and a biosensor device cooperating with the biosensor test strip to perform an assay, and the biosensor device comprising: a connector comprising a first side, a second side which is relative to the first side, a front end, two lateral sides, and an opening at the front end which is disposed between the first side and the second side of the connector for receiving the biosensor test strip,
   an ejection guiding groove disposed on the second side of the connector, wherein a front end of the ejection guiding groove communicating with the opening to contain one end of the biosensor test strip; and an electrical conductor formed of a unitary component made of metal, and attached to the front end, and two lateral sides of a body of the connector to prevent an electrical interference; and an ejection element cooperating with the ejection guiding groove and comprising an actuating part slidely disposed in the ejection guiding groove such that the actuating part positioned at a rear end of the ejection guiding groove before ejecting the biosensor test strip and the actuating part positioned at the front end of the ejection guiding groove after ejecting the biosensor test strip.

* * * * *